(12) United States Patent
Young et al.

(10) Patent No.: US 12,295,775 B2
(45) Date of Patent: May 13, 2025

(54) X-RAY IMAGING SYSTEM

(71) Applicant: KONINKLIJKE PHILIPS N.V., Eindhoven (NL)

(72) Inventors: Stewart Matthew Young, Hamburg (DE); Benjamin Hawellek, Hamburg (DE); Thomas Rohse, Braak (DE); Nataly Wieberneit, Hamburg (DE); Christina Textor, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 283 days.

(21) Appl. No.: 18/010,224

(22) PCT Filed: Jun. 10, 2021

(86) PCT No.: PCT/EP2021/065583
§ 371 (c)(1),
(2) Date: Dec. 14, 2022

(87) PCT Pub. No.: WO2021/254860
PCT Pub. Date: Dec. 23, 2021

(65) Prior Publication Data
US 2023/0248328 A1 Aug. 10, 2023

(30) Foreign Application Priority Data
Jun. 15, 2020 (EP) .................... 20179921

(51) Int. Cl.
*A61B 6/00* (2024.01)
(52) U.S. Cl.
CPC ............ *A61B 6/5217* (2013.01); *A61B 6/481* (2013.01); *A61B 6/482* (2013.01); *A61B 6/486* (2013.01); *A61B 6/5264* (2013.01); *A61B 6/54* (2013.01)

(58) Field of Classification Search
CPC ....... A61B 6/5217; A61B 6/481; A61B 6/482; A61B 6/486; A61B 6/5264; A61B 6/54; G16H 40/60; G16H 30/40
See application file for complete search history.

(56) References Cited

U.S. PATENT DOCUMENTS 11,325,188 B2 5/2022 McMurtry
2001/0007585 A1 7/2001 Nukui
(Continued)

FOREIGN PATENT DOCUMENTS

CN 104983436 A 10/2015
EP 3644273 A1 4/2020
(Continued)

OTHER PUBLICATIONS

PCT International Search Report, International application No. PCT/EP2021/65583, Sep. 17, 2021.
(Continued)

*Primary Examiner* — David P Porta
*Assistant Examiner* — Meenakshi S Sahu
(74) *Attorney, Agent, or Firm* — Larry Liberchuk

(57) ABSTRACT

The present invention relates to an X-ray imaging system (10), comprising: an X-ray image acquisition unit (20); and a processing unit (30). The processing unit is configured to instruct the X-ray image acquisition unit to carry out a sequence of scans of a body part of a patient. The X-ray image acquisition unit is configured to provide the processing unit with an X-ray image of the body part for a scan of the sequence of scans. The processing unit is configured to determine that the scan needs to be repeated, wherein the determination comprises analysis of the X-ray image of the body part. The processing unit is configured to determine that an action other than acquisition of the next scan in the scan sequence is required, wherein the determination com-
(Continued)

prises analysis of the X-ray image of the body part. The processing unit is configured to determine that the X-ray imaging unit is required to carry out the next scan in the scan sequence based on a determination that the scan does not need to be repeated and that an action other than acquisition of the next scan in the scan sequence is not required.

13 Claims, 2 Drawing Sheets

(56) References Cited

U.S. PATENT DOCUMENTS

| | | |
|---|---|---|
| 2013/0083978 A1 | 4/2013 | Frederick |
| 2019/0261938 A1 | 8/2019 | Sevenster |
| 2019/0320934 A1* | 10/2019 | Odry ................. A61B 5/7264 |
| 2019/0370958 A1* | 12/2019 | Hancu ................. G16H 30/40 |
| 2022/0301686 A1 | 9/2022 | Rohse |

FOREIGN PATENT DOCUMENTS

| | | |
|---|---|---|
| JP | 2005198798 A | 7/2005 |
| JP | 2007222311 A | 9/2007 |
| JP | 20200113694 A | 7/2020 |

OTHER PUBLICATIONS

Goosen A. et al., "Deep Learning for Pneumothorax Detection and Localization in Chest Radiographs", Image and Video Processing, Computer Vision and Pattern Recognition (cs.CV), MIDL 2019, London, United Kingdom, https://arxiv.org/abs/1907.07324.

* cited by examiner

X-RAY IMAGING SYSTEM

FIELD OF THE INVENTION

The present invention relates to an X-ray imaging system, to an X-ray imaging method, as well as to a computer program element and a computer readable medium.

BACKGROUND OF THE INVENTION

US2019/370958A1 describes, in certain implementations, a rule-based or deep learning-based approach capable of assessing diagnostic utility of images in near real time with respect to acquisition. It is described that an automated implementation of such an algorithm on the scanner would, in fact, emulate the doctor himself rating images in real time, and reduce the number of unneeded re-scans and recalls. It is described that it was found that diagnostic utility of an image is not an absolute measure, but instead depends upon the reading radiologist and the scan indication (i.e., the purpose of the scan), and that therefore, adapting the threshold (probability of an imaging volume to be deemed good) as a function of reading radiologist and scan indication can result in decreasing the number of re-scans and recalls.

US2019/320934A1 describes automated sequence prediction for a medical imaging session including a self-assessment mechanism. An initial scout sequence is performed of a patient or object. The initial scout sequence is validated. An abbreviated acquisition protocol is performed. The abbreviated acquisition protocol is validated. Additional sequences are performed. The sequences may also be configured based on the analysis of the previous scans using deep learning-based reasoning to select the next appropriate settings and procedures.

X-ray medical images are frequently taken in a scan sequence of a plurality of individual scans and exported in for example a DICOM format into a PACS system of a hospital for further evaluation. However, one or more of the scans may not be able to be reliably interpreted by a radiologist because they may not meet certain quality standards, requiring that the patient revisit the medical centre for repeat scans. Also, the radiologist may identify something within the scan sequence that requires a further examination that again requires the patient to visit a medical centre for a scan. These issues lead to time delays in effective diagnosis.

There is a need to address these issues.

SUMMARY OF THE INVENTION

It would be advantageous to improve X-ray imaging.

The object of the present invention is solved with the subject matter of the independent claims, wherein further embodiments are incorporated in the dependent claims. It should be noted that the following described aspects and examples of the invention apply also to the X-ray imaging system, to the X-ray imaging method, as well as for the computer program element and computer readable medium.

According to a first aspect, there is provided an X-ray imaging system, comprising:

an X-ray image acquisition unit; and
a processing unit.

The processing unit is configured to instruct the X-ray image acquisition unit to carry out a sequence of scans of a body part of a patient. The X-ray image acquisition unit is configured to provide the processing unit with an X-ray image of the body part for a scan of the sequence of scans. The processing unit is configured to determine that the scan needs to be repeated, wherein the determination comprises analysis of the X-ray image of the body part. The processing unit is configured to determine that an action other than acquisition of the next scan in the scan sequence is required, wherein the determination comprises analysis of the X-ray image of the body part. The processing unit is configured to determine that the X-ray imaging unit is required to carry out the next scan in the scan sequence based on a determination that the scan does not need to be repeated and that an action other than acquisition of the next scan in the scan sequence is not required.

In this manner, rather than progressing through a whole scan sequence on the scan sequence and being analysed off-line, individual scans are analysed in real time to provide feedback in terms of if that scan needs to be repeated, for example due to an image quality issue, or on the basis of the analysis of the image of that scan a different action is required, such as acquiring a different scan or even aborting the scan and carrying out another procedure if a particular medical condition was detected.

Thus, the processing unit can for example control an output unit to indicate to an operator that the last scan needs to be repeated, and the operator can then arrange for the last scan to be repeated. However, the processing unit itself can be in control X-ray image acquisition unit to automatically acquire the last scan again.

Thus, the processing unit can for example control the output unit to indicate to an operator that an action other than acquisition of the next scan in a scan sequence is required, and the operator can then arrange for that action to be carried out. However, the processing unit itself can be in control of the action other than acquisition of the next scan in a scan sequence and this be carried out in effect automatically.

Also, the processing unit can for example control the output unit to indicate to the operator that the next scan in a scan sequence is required, or in other words should be carried out. However, again the processing unit itself can control the X-ray image acquisition unit to carry out the next scan in the scan sequence automatically.

Thus, in an example the processing unit is configured to instruct the X-ray imaging unit to carry out the next scan in the scan sequence based on the determination that the scan does not need to be repeated and that an action other than acquisition of the next scan in the scan sequence is not required In an example, the determination that the scan needs to be repeated comprises analysis to determine that the X-ray image of the body part does not meet at least one image quality criteria.

Thus, the patient may have moved during the acquisition of a particular scan leading to blurring, or another issue may have arisen requiring that a repeat scan be undertaken. This can be done immediately rather than a determination at the end being made after the scan sequence has been acquired and processed, requiring that the patient return to the image acquisition unit and be rescanned.

In an example, the analysis of the X-ray image comprises utilization of at least one image processing algorithm.

In an example, the at least one image processing algorithm comprises one or more of a contrast determination algorithm and a blur determination algorithm.

In an example, the determination of the action other than acquisition of the next scan in the scan sequence comprises a determination that the X-ray image acquisition unit carry out a different scan to that in the scan sequence.

Thus for example a determination can be made that a medical condition not previously recognised has been identified, or at least suspected to exist, and a different scan can then be performed, for example at a different orientation and/or at a different energy in order to aid in confirming such a diagnosis.

In an example, the different scan comprises a scan at a different X-ray energy to the last scan.

In an example, the different scan comprises a scan at a different orientation through the body part to the last scan.

In an example, the determination of the action other than acquisition of the next scan in the scan sequence comprises a determination that the patient be moved.

Thus for example it could be determined that a patient be moved in order to enable a different view through the body part to be acquired, or that the patient be moved in order to displace fluids for example, or image be acquired for bone metastasis for example.

In an example, the determination of the action other than acquisition of the next scan in the scan sequence comprises a determination that a medical procedure be carried out on the patient.

In an example, the determination of the action other than acquisition of the next scan in the scan sequence comprises a determination that the scan sequence be stopped.

In other words, it could be established on the basis of the last scan that immediate action is required over and above the scan being performed, requiring that for example the scan sequence we stopped and the patient undergo an immediate medical procedure.

In an example, the determination that the action other than acquisition of the next scan in the scan sequence is required comprises analysis to determine a medical condition.

In an example, the determination that the action other than acquisition of the next scan in the scan sequence is required comprises utilization of a trained machine learning algorithm.

Thus for example a deep learning algorithm such as a convolutional neural network trained in a whole series of image scans and associated ground truth data regarding different medical conditions, can be utilised to determine from the image scan if a specific action such as acquiring a different scan should be performed rather than going onto the next scan in the scan sequence.

According to a second aspect, there is provided an X-ray imaging method, comprising:
 a) instructing by a processing unit an X-ray image acquisition unit to carry out a scan of a sequence of scans of a body part of a patient;
 b) providing the processing unit with an X-ray image of the body part for the scan;
 c) determining by the processing unit that the scan needs to be repeated, wherein the determining comprises analysis of the X-ray image of the body part; or
 d) determining by the processing unit that an action other than acquisition of the next scan in the scan sequence is required, wherein the determining comprises analysis of the X-ray image of the body part; or
 e) determining by the processing unit that the X-ray imaging unit is required to carry out the next scan in the scan sequence.

The equivalent of steps c) or d) can be performed with respect to the next scan and associated image to be acquired as a consequence of step e).

According to another aspect, there is provided a computer program element controlling a system as previously described which, if the computer program element is executed by a processing unit, is adapted to perform the method steps as previously described.

According to another aspect, there is provided a computer readable medium having stored computer element as previously described.

The computer program element, can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
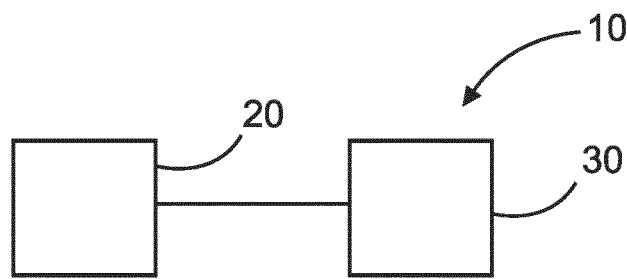
FIG. 1 shows a schematic set up of an example of an X-ray imaging system.

FIG. 1 shows a schematic example of an X-ray imaging system 10. The system 10 comprises an X-ray image acquisition unit 20, and a processing unit 30. The processing unit is configured to instruct the X-ray image acquisition unit to carry out a sequence of scans of a body part of a patient. The X-ray image acquisition unit is configured to provide the processing unit with an X-ray image of the body part for a scan of the sequence of scans. The processing unit is configured to determine that the scan needs to be repeated. The determination that the scan needs to be repeated comprises analysis of the X-ray image of the body part. The processing unit is configured to determine that an action other than acquisition of the next scan in the scan sequence is required. The determination that an action other than acquisition of the next scan in the scan sequence is required comprises analysis of the X-ray image of the body part. The processing unit is configured to determine that the X-ray imaging unit is required to carry out the next scan in the scan sequence based on a determination that the scan does not need to be repeated and that an action other than acquisition of the next scan in the scan sequence is not required.

In an example, the processing unit is configured to automatically control the X-ray image acquisition unit to repeat the scan, based on the determination that the scan needs to be repeated.

In an example, the processing unit is configured to control an output unit to output an indication that the last scan be repeated, based on the determination that the scan needs to be repeated.

In an example, the processing unit is configured to automatically control the carrying out of the action other than acquisition of the next scan in the scan sequence, based on the determination that an action other than acquisition of the next scan in the scan sequence is required.

In an example, the processing unit is configured to control the output unit to output an indication that the action other than acquisition of the next scan in the scan sequence is required, based on the determination that an action other than acquisition of the next scan in the scan sequence is required.

In an example, the processing unit is configured to automatically control the X-ray imaging unit to carry out the next scan in the scan sequence based on the determination that the scan does not need to be repeated and that an action other than acquisition of the next scan in the scan sequence is not required.

In an example, the processing unit is configured to control the output unit to output an indication that the next scan in the scan sequence should be carried out, based on the determination that the scan does not need to be repeated and that an action other than acquisition of the next scan in the scan sequence is not required.

In an example, the X-ray image acquisition unit is configured to provide the X-ray image of the body part to a visual display screen.

In an example, the X-ray image is provided to the processing unit at substantially the same time as it is provided to the visual display.

Thus at the same time that the processing unit makes a determination that a repeat scan should be acquired or that different action be undertaken or that the next scan in the scan sequence be acquired, a user of the system is provided with the image upon which the processing unit is making this determination. This enables, the user to override the system if it is determined that the image is of good enough quality, or that determined other action is not actually required, and also enables the user to perform the other action, such as moving the patient or setting up the system for a different scan.

According to an example, the determination that the scan needs to be repeated comprises analysis to determine that the X-ray image of the body part does not meet at least one image quality criteria.

According to an example, the analysis of the X-ray image comprises utilization of at least one image processing algorithm.

According to an example, the at least one image processing algorithm comprises one or more of a contrast determination algorithm and a blur determination algorithm.

According to an example, the determination of the action other than acquisition of the next scan in the scan sequence comprises a determination that the X-ray image acquisition unit carry out a different scan to that in the scan sequence.

According to an example, the different scan comprises a scan at a different X-ray energy to the last scan.

According to an example, the different scan comprises a scan at a different orientation through the body part to the last scan.

According to an example, the determination of the action other than acquisition of the next scan in the scan sequence comprises a determination that the patient be moved.

According to an example, the determination of the action other than acquisition of the next scan in the scan sequence comprises a determination that a medical procedure be carried out on the patient.

According to an example, the determination of the action other than acquisition of the next scan in the scan sequence comprises a determination that the scan sequence be stopped.

According to an example, the determination that the action other than acquisition of the next scan in the scan sequence is required comprises analysis to determine a medical condition.

According to an example, the determination that the action other than acquisition of the next scan in the scan sequence is required comprises utilization of a trained machine learning algorithm.

Figure 2:
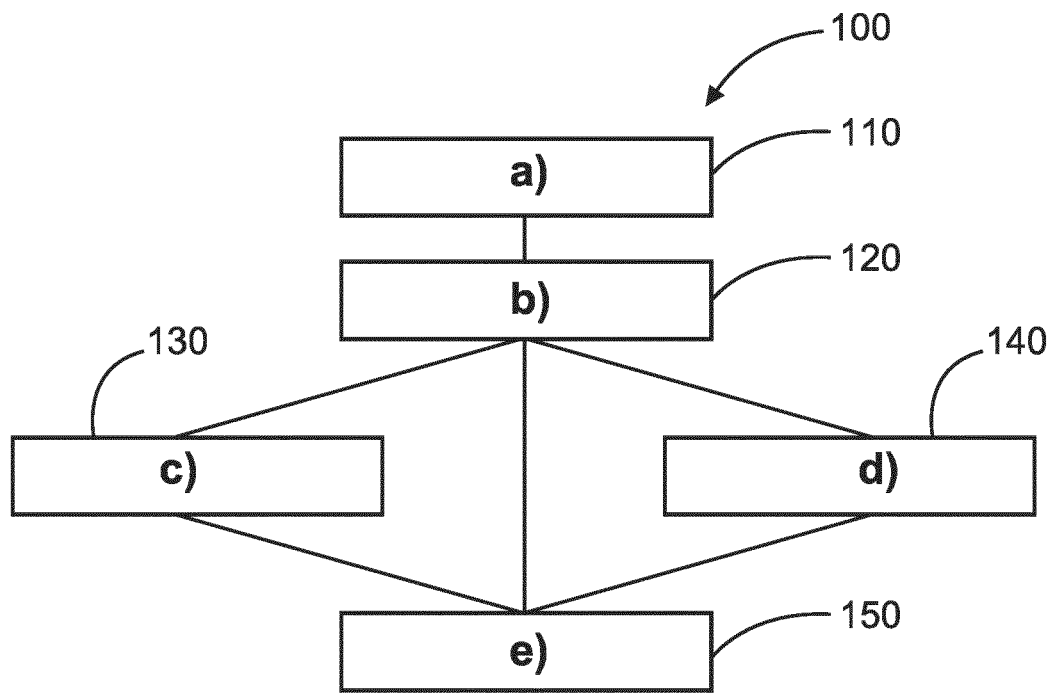
FIG. 2 shows an X-ray imaging method.

FIG. 2 shows an X-ray imaging method 100 in its basic steps. The method 100 comprises:

in an instructing step 110, also referred to as step a), instructing by a processing unit an X-ray image acquisition unit to carry out a scan of a sequence of scans of a body part of a patient;

in a providing step 120, also referred to as step b), providing the processing unit with an X-ray image of the body part for the scan;

in a determining step 130, also referred to as step c), determining by the processing unit that the scan needs to be repeated, wherein the determining comprises analysis of the X-ray image of the body part; or in a determining step 140, also referred to as step d), determining by the processing unit that an action other than acquisition of the next scan in the scan sequence is required, wherein the determining comprises analysis of the X-ray image of the body part; or in a determining step 150, also referred to as step e) determining by the processing unit that the X-ray imaging unit is required to carry out the next scan in the scan sequence.

In an example, step c) comprises automatically controlling by the processing unit the X-ray image acquisition unit to repeat the scan, based on the determination that the scan needs to be repeated.

In an example, step c) comprises controlling by the processing unit an output unit to output an indication that the last scan be repeated, based on the determination that the scan needs to be repeated.

In an example, step d) comprises automatically controlling by the processing unit the carrying out of the action other than acquisition of the next scan in the scan sequence, based on the determination that an action other than acquisition of the next scan in the scan sequence is required.

In an example, step d) comprises controlling by the processing unit the output unit to output an indication that the action other than acquisition of the next scan in the scan sequence is required, based on the determination that an action other than acquisition of the next scan in the scan sequence is required.

In an example, step e) comprises automatically controlling by the processing unit the X-ray imaging unit to carry out the next scan in the scan sequence based on the determination that the scan does not need to be repeated and that an action other than acquisition of the next scan in the scan sequence is not required.

In an example, step e) comprises controlling by the processing unit the output unit to output an indication that the next scan in the scan sequence should be carried out, based on the determination that the scan does not need to be repeated and that an action other than acquisition of the next scan in the scan sequence is not required.

In an example, step c) comprises analysis to determine that the X-ray image of the body part does not meet at least one image quality criteria.

In an example, the analysis of the X-ray image comprises utilization of at least one image processing algorithm.

In an example, the at least one image processing algorithm comprises one or more of a contrast determination algorithm and a blur determination algorithm.

In an example, in step d) the determining the action other than acquisition of the next scan in the scan sequence comprises determining that the X-ray image acquisition unit carry out a different scan to that in the scan sequence.

In an example, the different scan comprises a scan at a different X-ray energy to the last scan.

In an example, the different scan comprises a scan at a different orientation through the body part to the last scan.

In an example, in step d) the determining the action other than acquisition of the next scan in the scan sequence comprises determining that the patient be moved.

In an example, in step d) the determining the action other than acquisition of the next scan in the scan sequence comprises determining that a medical procedure be carried out on the patient.

In an example, in step d) the determining the action other than acquisition of the next scan in the scan sequence comprises determining that the scan sequence be stopped.

In an example, in step d) the determining that the action other than acquisition of the next scan in the scan sequence is required comprises analysis to determine a medical condition.

In an example, in step d) the determining that the action other than acquisition of the next scan in the scan sequence is required comprises utilizing a trained machine learning algorithm.

Figure 3:
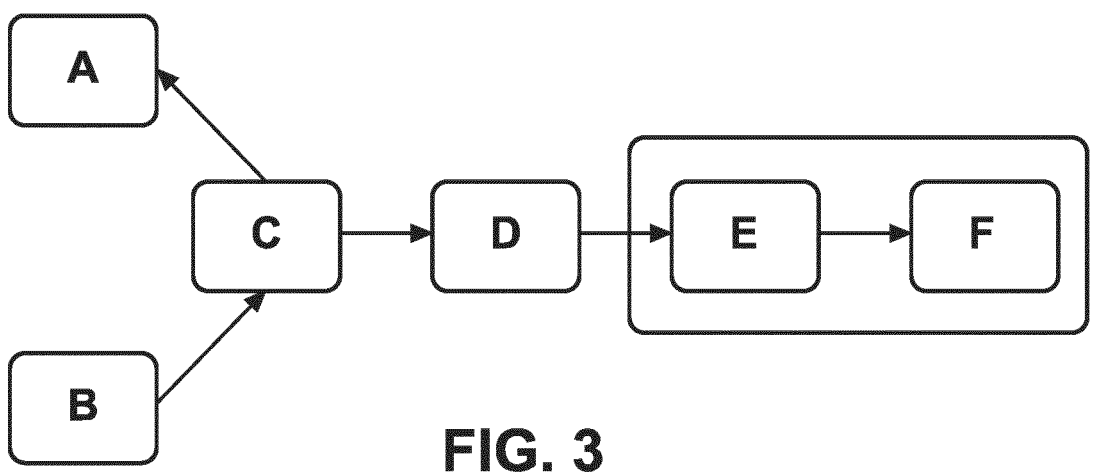
FIG. 3 shows a schematic overview of a detailed implementation of an exemplar X-ray imaging system.
Figure 4:
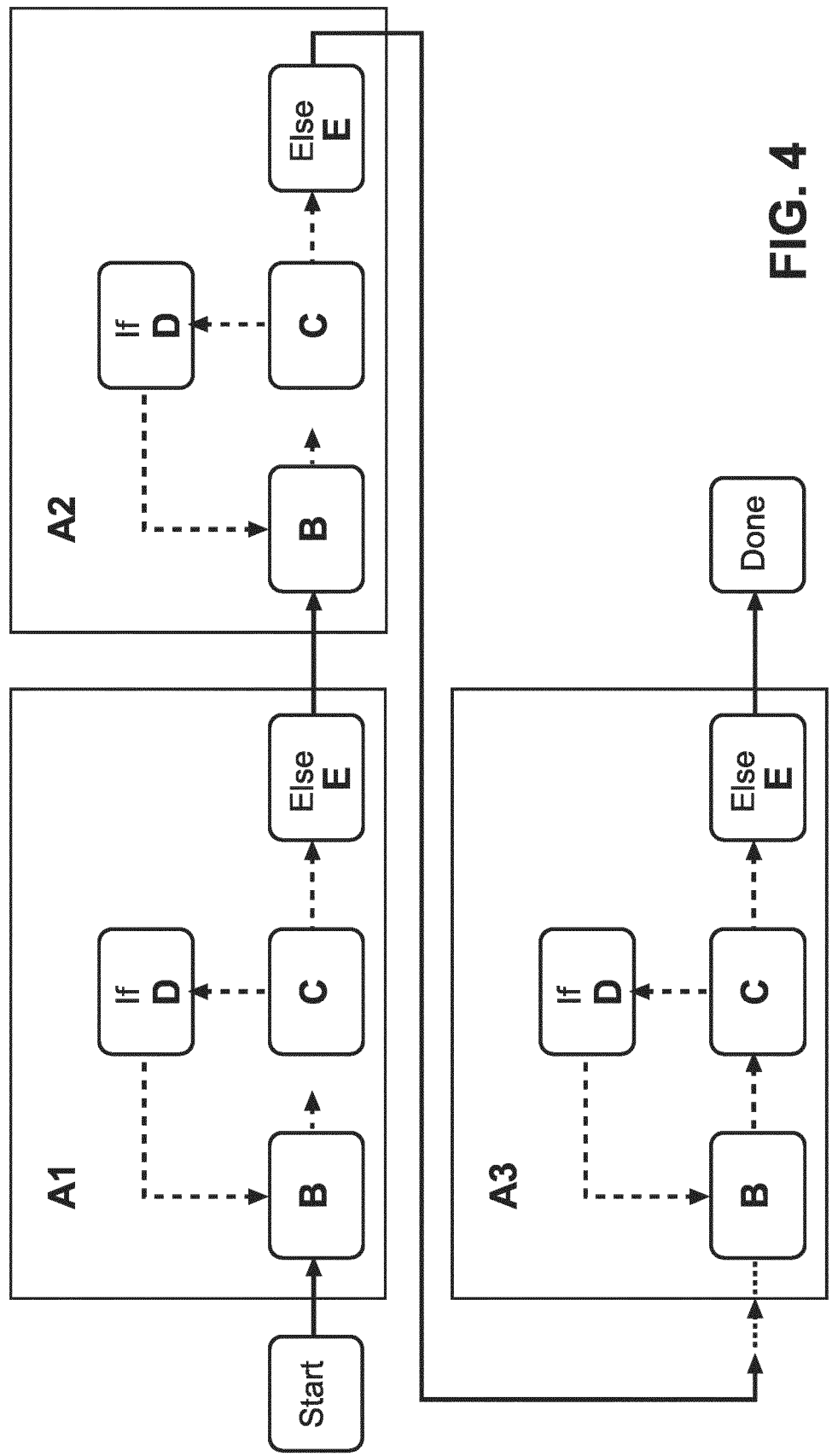
FIG. 4 shows a schematic overview of a detailed implementation of an exemplar X-ray imaging method.

The X-ray imaging system and X-ray imaging method are now described with respect to specific embodiments, where reference is made to FIGS. 3-4.

To set the scene for the new developments, a current typical workflow for an existing X-ray imaging system is described. The typical workflow on current Digital X-ray (DXR) imaging systems is that "image series" or "scan sequence" (a set of one or more images of the same patient) is "completed" prior to the export of these images e.g. in DICOM format to the PACS system of the hospital for further evaluation. This workflow step is typically performed by clicking a button in the UI, at the time-point when acquisition of all images intended in the series has been completed. This "complete" click triggers an export of the images to the PACS for further evaluation. For a system designed to provide immediate feedback, which is independent of the acquisition system (vendor-controlled PC and monitor), and thus connected to the acquisition system via e.g. the network, this means that the images are only available for further evaluation at a time-point dependent upon the completion of the image series, and not necessarily immediately after the image acquisition when the feedback is actually required. The new development described here addresses this.

FIG. 3 shows a schematic overview of the functional parts or steps of a new X-ray imaging system and associated method. In order to circumvent the problem of a clinical PACS integration, and to provide a vendor independent solution. In FIG. 3 a console monitor is represented by "A", a console PC is represented by "B", a signal splitter is represented by "C", a frame grabber is represented by "D", a frame analyzer is represented by "E", and an image analyzer is represented by "F".

With respect to FIG. 3 in a detailed embodiment the following functional steps and associated component parts are utilized:

Use a signal splitter and a frame-grabber,
Analyse the contents of the console display (screen) of the imaging modality to search for the medical image in the monitor signal and
Evaluate the image for image aspects which may require immediate feedback, for example if image quality of the acquired medical image does not meet with certain quality standards.

In an example, the above functional steps and modules are embedded into the imaging workflow as illustrated in FIG. 3. In this way clinical images are displayed on the monitor of the console of the imaging equipment and are automatically and immediately detected within the image stream provided by the frame-grabber, and then passed to the image analyser, thereby enabling the possibility of an immediate feedback directly after acquisition of a specific image. This "immediate feedback loop" can occur immediately after the acquisition of each individual image within any "image series", and specifically before the "complete" step required by the UI of the imaging equipment. It is to be noted that the images need not be shown on a monitor and that a signal splitter is not actually required. Also, a frame grabber and associated image evaluation or analysis can be automatically carried out on the latest image as it is acquired, and as such there does not need to be a frame grabber as such.

FIG. 4 then provides a schematic overview of the how such "immediate feedback" is, in a specific example, directly integrated into the workflow of an improved imaging workflow. In FIG. 4 each box A1, A2 and A3 represented an "immediate Feedback Loop". In each loop an image is represented by "B", and "analyse and provide feedback" step is represented by "C". Step "D" represented a logical "IF" step relating to "if there are implications for the work flow" then a new image (repeat scan or completely new image) is acquired. Step "E" represents a logical "ELSE" step, where the scan sequence continues, and the process is repeated for each scan of the scan sequence.

In summary the steps in a specific embodiment are:

A signal splitter able to generate identical copies of the signal to be displayed on the computer screen of the console monitor.

A frame grabber which provides individual images identical to those displayed on the computer screen A frame analyser which looks for a medical image in the series of frames provided by the frame grabber, and able to:
Recognise Specific Radiograph Images within the Frames
Identify relevant time-points at which immediate feedback could be required within the series of frames.

An image analyser which performs an analysis of the image to determine whether an immediate feedback should be provided to the user of the imaging equipment.

A means to display the immediate feedback to the user of the imaging equipment, for example using a tablet display device located close to the console monitor.

Thus, the feedback is provided to the user independent of any user interaction, and very rapidly after the appearance of the image upon the console of the imaging equipment. Regarding, the automatic evaluation deep learning based algorithms can be utilized. An example of such a deep learning algorithm is described in: "*Deep Learning for Pneumothorax Detection and Localization in Chest Radiographs*", A. Gooßen, H. Deshpande, T. Harder, E. Schwab, I. Baltruschat, T. Mabotuwana, N. Cross, A. Saalbach, MIDL 2019, London, United Kingdom, https://arxiv.org/abs/1907.07324

An exemplar medical condition that can trigger that a new scan be acquired is Pneumothorax, and where for example deep learning algorithms/techniques that analyse imagery to determine if a medical condition could be indicated in the imagery can include:

convolutional neural networks,
multiple-instance learning, and
fully convolutional networks.

Regarding implementing the new technology, signal splitting and frame grabbing hardware are currently available, and can even be embodied in a single piece of hardware. Also, an X-ray system can have a DXR console with a User Interface. In the frame a single image (such as PA projection view) is displayed in the main viewport. There will also be in the UI placeholders for further images, which are to be acquired in the image series. These may appear later in the series obtained by the frame-grabber, once the radiographer has proceeded in their workflow. The image analyser module contains a logic able to identify these relevant time-points within the image series from the frame-grabber, and thereby provide immediate feedback only at appropriate time-points.

Thus, beside quality analysis of the acquired medical image an automatic diagnosis can be performed on the image analyser and the urgency of a medical treatment could be proposed (critical findings). Furthermore, the analyser can provide an easy way to consult a colleague for a second opinion.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system, comprising:
an X-ray image acquisition unit configured to carry out a sequence of scans of a body part and to provide an X-ray image of the body part for a scan of the sequence of scans; and
a processor configured to:
determine that the scan needs to be repeated, wherein the determination comprises analysis of the X-ray image of the body part;
determine that an action other than acquisition of the next scan in the scan sequence is required, wherein the determination comprises analysis of the X-ray image of the body part; and
determine that the X-ray imaging unit is required to carry out the next scan in the scan sequence based on a determination that the scan does not need to be repeated and that an action other than acquisition of the next scan in the scan sequence is not required.

2. The system according to claim 1, wherein the determination that the scan needs to be repeated comprises analysis to determine that the X-ray image of the body part does not meet at least one image quality criteria.

3. The system according to claim 2, wherein the analysis of the X-ray image comprises utilization of at least one image processing algorithm.

4. The system according to claim 3, wherein the at least one image processing algorithm comprises one or more of: a contrast determination algorithm and a blur determination algorithm.

5. The system according to claim 1, wherein the determination of the action other than acquisition of the next scan in the scan sequence comprises a determination that the X-ray image acquisition unit carry out a different scan in the scan sequence.

6. The system according to claim 5, wherein the different scan comprises a scan at a different X-ray energy from the last scan.

7. The system according to claim 5, wherein the different scan comprises a scan at a different orientation through the body part from the last scan.

8. The system according to claim 1, wherein the determination of the action other than acquisition of the next scan in the scan sequence comprises a determination that a patient be moved.

9. The system according to claim 1, wherein the determination of the action other than acquisition of the next scan in the scan sequence comprises a determination that a medical procedure be carried out on a patient.

10. The system according to claim 1, wherein the determination of the action other than acquisition of the next scan in the scan sequence comprises a determination that the scan sequence be stopped.

11. The system according to claim 1, wherein the determination that the action other than acquisition of the next scan in the scan sequence is required comprises analysis to determine a medical condition.

12. The system according to claim 1, wherein the determination that the action other than acquisition of the next scan in the scan sequence is required comprises utilization of a trained machine learning algorithm.

13. An X-ray imaging method, comprising:
   instructing an X-ray image acquisition unit to carry out a scan of a sequence of scans of a body part of a patient;
   providing an X-ray image of the body part for the scan;
   determining unit that the scan needs to be repeated, wherein the determining comprises analysis of the X-ray image of the body part; or
   determining that an action other than acquisition of the next scan in the scan sequence is required, wherein the determining comprises analysis of the X-ray image of the body part; or
   determining that the X-ray imaging unit is required to carry out the next scan in the scan sequence.

* * * * *